(12) United States Patent
De Vries et al.

(10) Patent No.: US 10,293,178 B2
(45) Date of Patent: May 21, 2019

(54) BRACHYTHERAPY POSITION VERIFICATION SYSTEM AND METHODS OF USE

(71) Applicant: Nucletron Operations B.V., Veenendaal (NL)

(72) Inventors: Frits De Vries, Veenendaal (NL); Adriaan Van Appeldoorn, Veenendaal (NL)

(73) Assignee: Nucletron Operations B.V., Veenendaal (NL)

( * ) Notice: Subject to any disclaimer, the term of this patent is extended or adjusted under 35 U.S.C. 154(b) by 1128 days.

(21) Appl. No.: 14/565,807

(22) Filed: Dec. 10, 2014

(65) Prior Publication Data

US 2016/0166328 A1    Jun. 16, 2016

(51) Int. Cl.
*A61B 19/00*    (2006.01)
*A61N 5/10*    (2006.01)
(Continued)

(52) U.S. Cl.
CPC ...... *A61N 5/1001* (2013.01); *A61B 17/00234* (2013.01); *A61B 19/5202* (2013.01);
(Continued)

(58) Field of Classification Search
None
See application file for complete search history.

(56) References Cited

U.S. PATENT DOCUMENTS 6,320,935 B1    11/2001    Shinar et al.
6,458,068 B1    10/2002    Ellard et al.
(Continued)

FOREIGN PATENT DOCUMENTS

| EP | 1 272 862 | 1/2005 |
|---|---|---|
| WO | WO 2008/009917 | 1/2008 |
| WO | WO-2011/080606 A1 | 7/2011 |
| WO | WO-2014/049477 A1 | 4/2014 |

OTHER PUBLICATIONS

European Patent Office Search Report for Application No. 15199304.5, dated Apr. 14, 2016 (6 pages).

*Primary Examiner* — Angela M Hoffa
*Assistant Examiner* — Vani Gupta
(74) *Attorney, Agent, or Firm* — Bookoff McAndrews, PLLC

(57) ABSTRACT

In one embodiment, a verification system for confirming the position of a conduit inserted within a patient may include an elongate control element dimensioned for insertion within the conduit. The control element has a proximal end and a distal end, and a verification element coupled to a distal region. The verification element may be configured to detect the presence of a reference marker associated with the conduit and communicate a signal indicative of the position of the reference marker relative to the verification element. The control element may also be configured to maneuver the verification element along a length of the conduit. The system may also include a drive device coupled to a proximal region of the control element for controlling movement of the control element through the conduit, a controller associated with the verification element and configured to communicate with the verification element, and a signal conductor for conducting the signal between the verification element and the controller.

25 Claims, 15 Drawing Sheets

(51) Int. Cl.
    *A61B 17/00* (2006.01)
    *A61B 34/20* (2016.01)
    *A61B 90/00* (2016.01)

(52) U.S. Cl.
    CPC .......... *A61B 19/5244* (2013.01); *A61B 19/54* (2013.01); *A61B 34/20* (2016.02); *A61N 5/1039* (2013.01); *A61N 5/1048* (2013.01); *A61N 5/1075* (2013.01); *A61B 2017/00323* (2013.01); *A61B 2019/521* (2013.01); *A61B 2019/5236* (2013.01); *A61B 2019/5238* (2013.01); *A61B 2019/5251* (2013.01); *A61B 2019/5255* (2013.01); *A61B 2019/5276* (2013.01); *A61B 2019/5437* (2013.01); *A61B 2019/5483* (2013.01); *A61B 2090/3983* (2016.02); *A61N 5/1002* (2013.01); *A61N 5/103* (2013.01); *A61N 5/1007* (2013.01); *A61N 5/1014* (2013.01); *A61N 5/1015* (2013.01); *A61N 5/1016* (2013.01); *A61N 5/1017* (2013.01); *A61N 5/1027* (2013.01); *A61N 5/1028* (2013.01); *A61N 5/1029* (2013.01); *A61N 2005/1008* (2013.01); *A61N 2005/1051* (2013.01)

(56) References Cited

U.S. PATENT DOCUMENTS

| | | | |
|---|---|---|---|
| 6,615,070 B2 | 9/2003 | Lee | |
| 7,107,089 B2 | 9/2006 | Lee | |
| 7,662,083 B2 | 2/2010 | Gueye et al. | |
| 8,133,167 B2 | 3/2012 | Gueye et al. | |
| 8,231,516 B2 | 7/2012 | Maschke | |
| 2006/0135843 A1* | 6/2006 | Heath | A61N 5/1007 600/7 |
| 2008/0319341 A1* | 12/2008 | Taylor | A61B 10/0275 600/567 |
| 2010/0152521 A1* | 6/2010 | Price | A61N 5/1027 600/7 |
| 2013/0072753 A1 | 3/2013 | Zappia et al. | |
| 2013/0204072 A1* | 8/2013 | Verard | A61N 5/1027 600/8 |
| 2013/0303902 A1* | 11/2013 | Smith | A61B 6/12 600/431 |
| 2014/0114115 A1* | 4/2014 | Krechting | A61N 5/1048 600/3 |
| 2015/0327949 A1* | 11/2015 | Van De Wardt | A61N 5/1007 600/417 |

* cited by examiner

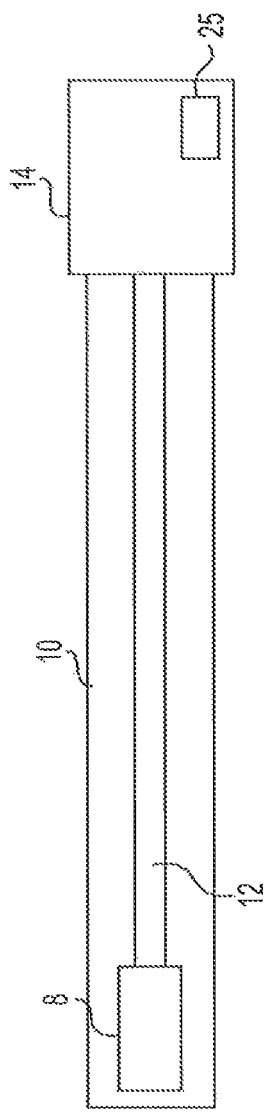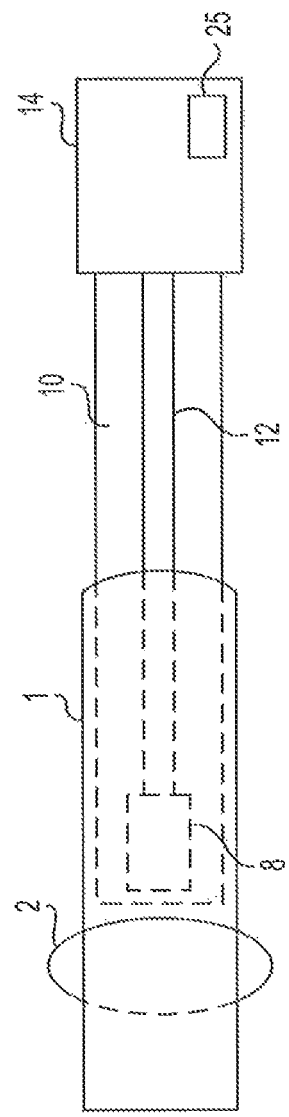
FIG. 5A
FIG. 5B

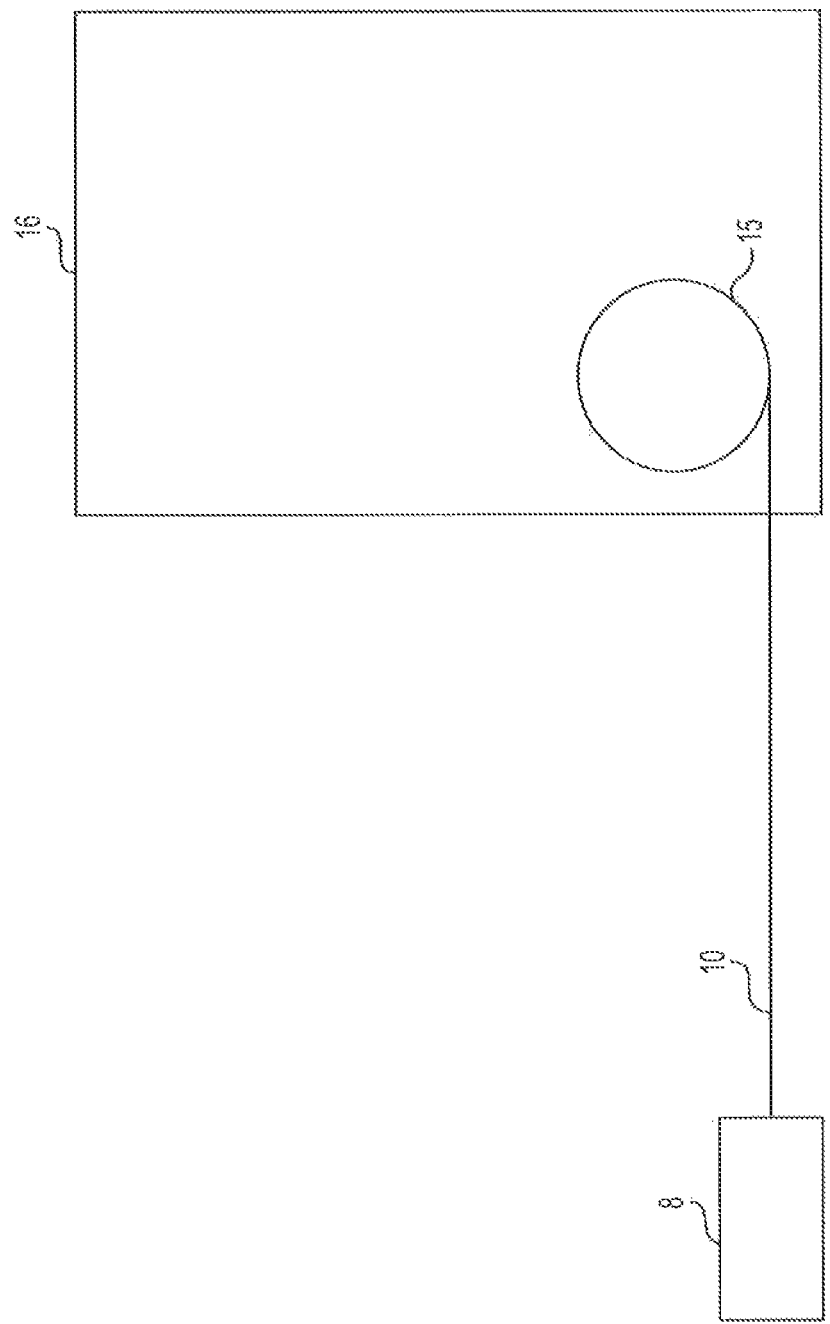

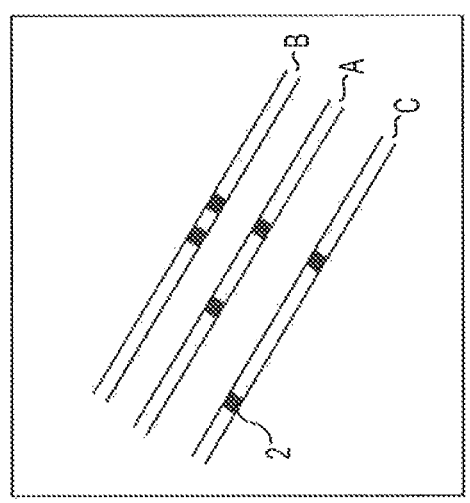
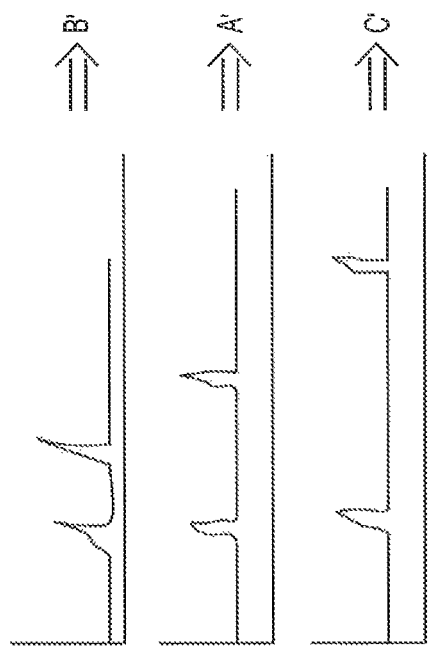
FIG. 7A
FIG. 7B

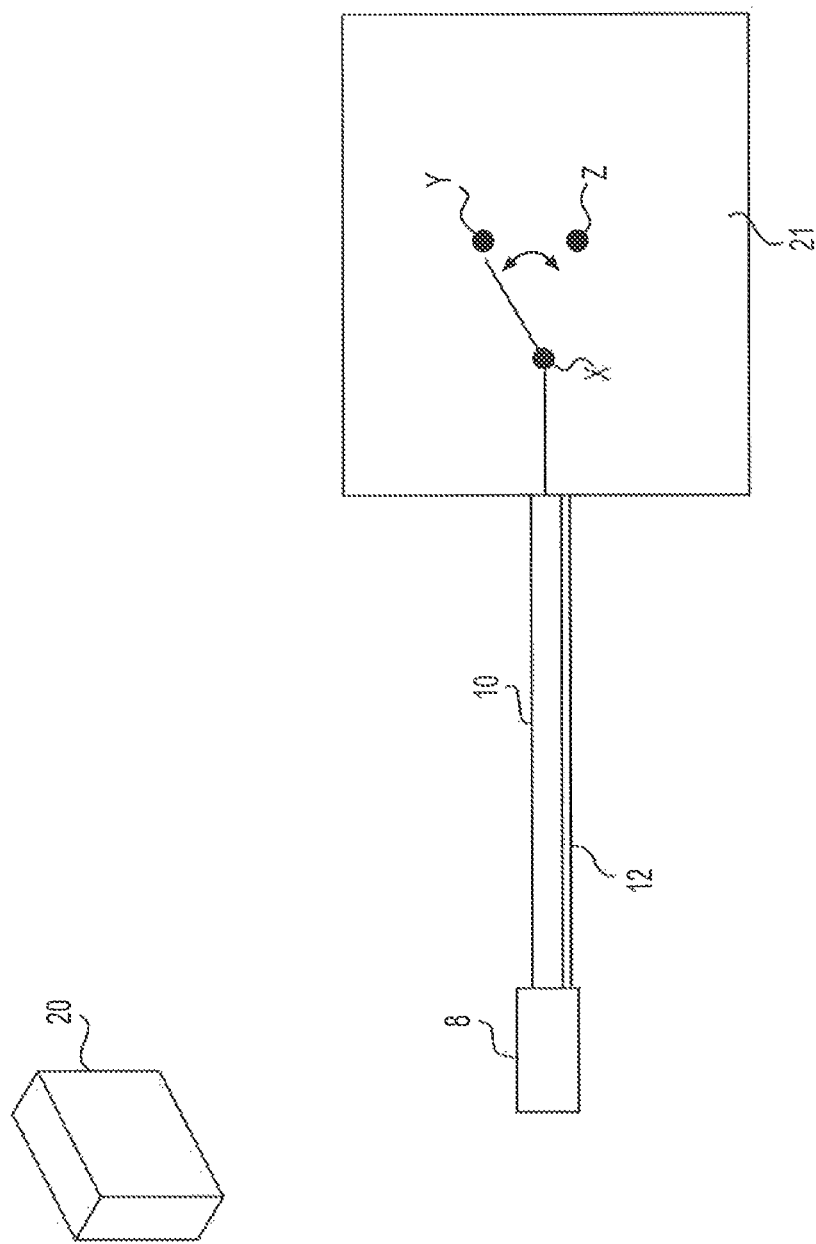

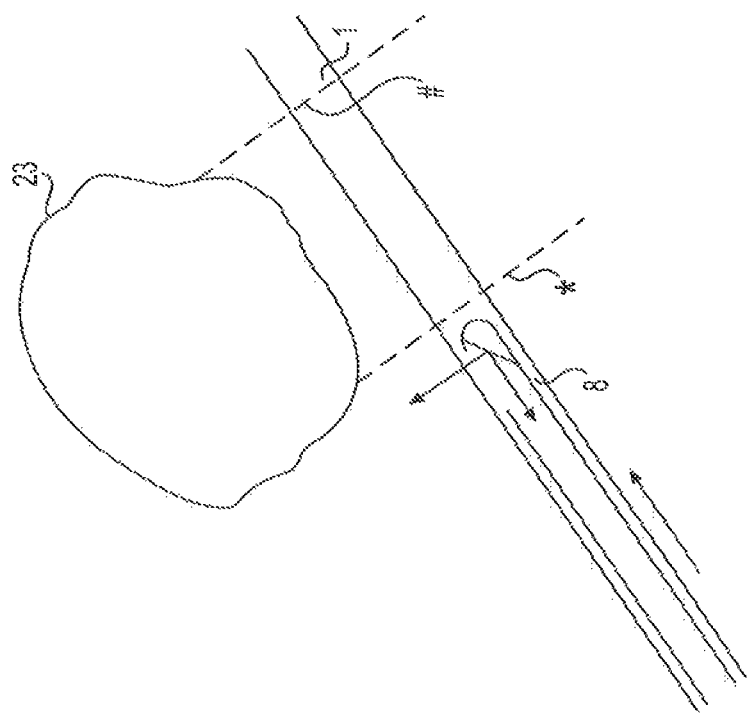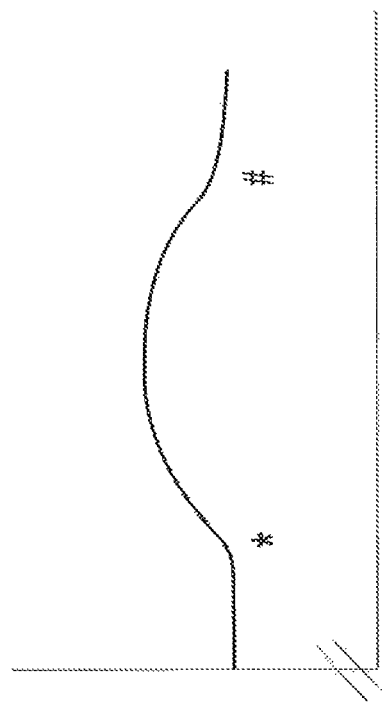

BRACHYTHERAPY POSITION VERIFICATION SYSTEM AND METHODS OF USE

TECHNICAL FIELD

Embodiments of the present disclosure relate to position verification systems, and more particularly, to brachytherapy systems for verifying the positioning of a conduit configured to receive a radiotherapy source once the conduit is within a patient.

BACKGROUND INFORMATION

Brachytherapy is a method of treating cancer by placing one or more radiotherapy sources in or by an area of tissue requiring treatment. Delivering radiation directly and accurately to the target treatment area may allow a clinician to administer higher doses of radiation while decreasing the impact on surrounding, healthy tissue.

In a typical brachytherapy treatment method, prior to treatment delivery, one or more conduits, for example, a brachytherapy applicator, a needle, a tube, or a catheter, is positioned within a target treatment area. The conduit is connected to a source of treatment, and a radiotherapy source is delivered from the treatment source and through the conduit into the treatment area. The conduits are positioned within the patient to deliver the radiotherapy source to suitable, pre-determined treatment locations. The treatment source may be a mechatronic or computerized device (e.g., an afterloader), or the treatment may be delivered manually, and the radiotherapy source may either be a small X-ray generating device, a high dose-rate radioactive source, or a low dose-rate radioactive source for use with longer, shorter, or even permanent dwelling times within the patient.

To increase the effectiveness of brachytherapy, clinicians aim to administer an optimal dosage of radiotherapy source to the target tissue. Following diagnosis, brachytherapy treatment may include multiple stages. Imaging of the patient anatomy and disease anatomy (e.g., tumor location, size, shape, density, orientation) may be analyzed to determine the appropriate regions to administer treatment to. During a treatment preparation and/or planning stage, the desired placement, positioning, and orientation of one or more conduits to deliver the treatment to these target treatment regions may then be determined. Additionally, one or more dwell positions (i.e., locations where the radiotherapy source will remain for a period of time) within each conduit may be mapped in order to achieve a desired dose distribution. During these stages, conduits, which may take the form of an applicator (e.g., having one or more individual conduit channels), needles, tubes, or catheters, may be inserted into a patient, and imaging may be used to confirm the position of the conduits. Next, during a treatment delivery stage, one or more radiotherapy sources may be delivered to the conduits, and the patient may undergo radiation treatment.

Movement or misalignment of one or more conduits may affect the amount of radiation treatment delivered to the target tissue. Misalignment could cause delivery of treatment to the wrong area or delivery of the wrong dosage of treatment to the target area. Yet, there is often no convenient way to verify positioning of the conduits after the treatment preparation/planning stage to confirm that the treatment will be delivered as planned.

For example, an applicator may be inserted into a patient for treatment planning, and medical imaging may be used to assess positioning of the conduits. Based on this information, a healthcare provider may determine the location of the dwell positions. Imaging and/or tracking devices and/or processing software may be used to assist with the treatment planning based on the location of the applicator within the body. Once treatment preparation and planning are complete, the patient may be moved into a different room for treatment delivery or otherwise prepared for treatment delivery. The treatment delivery room may include shielding to accommodate use of radioactive materials and may not be compatible with the imaging and/or tracking devices used during treatment planning. Accordingly, the treatment delivery system (e.g., afterloader) may determine radiotherapy source positioning based on indirect measurements, such as the predetermined dwell positions, saved imaging data, the length of the conduits, the distance that the source has been inserted into the conduits, and the connection of transfer tubes to the conduits. Yet, inaccuracies may occur when relying on secondary measurements. For example, any snaking, bunching, or slack that may be created as a wire with a source or sensor is fed into the conduit may result in inaccurate determinations of how far the source or sensor has been inserted and where in the conduit it is located. Thus, following insertion of the conduit into the body for treatment planning purposes, the conduit may shift within the body, and current systems may not be able to directly determine spatial positioning of the conduit. Consequently, current systems may be unable to directly or accurately verify the ultimate location of the radiotherapy source when delivered to the conduit. Shifting of the conduit after the imaging during treatment planning or preparation may go undetected, resulting in inaccurate radiation treatment for the patient.

Additionally, it may be difficult or impossible to synchronize positioning data across the various systems, resulting in potential undetected discrepancies or inefficiencies. For example, treatment delivery systems, such as afterloaders, may use one-dimensional data, like dwell positions, the number of conduits, and/or the length of the conduits, to determine positioning. Image processing/planning software may use image data to create their own position definitions. Three-dimensional tracking systems, such as electromagnetic tracking, optical tracking, and other multiple degrees-of-freedom sensor systems may use references and may determine positioning based on relative measurements and/or calibration. Because each system measures positional information differently, it may be difficult, if not impossible, to merge or synchronize this data.

Further, current methods of position verification, including medical imaging (e.g., radiography, X-ray, MRI, ultrasound), electromagnetic tracking, optical shape sensing, or in vivo dosimetry may be expensive, complex, unwieldy, may disturb the workflow, or may cause harm or discomfort to the patient. Additionally, these devices may not be integrated into the treatment delivery system and consequently their feedback cannot be easily or safely used to interrupt or adjust treatment delivery if an inconsistency is detected as treatment occurs.

Additionally, multiple catheters or needles may be inserted into a patient or an applicator may include multiple conduit channels. Each conduit may have unique shapes, lengths, sizes, etc., and each conduit may need to be connected to an afterloader in a specific orientation in order to deliver the radiotherapy source to the target treatment location in accordance with the treatment planning. Unintentionally switching one or more transfer tubes when connecting the conduits to the afterloader for treatment delivery may thus result in wrong or inaccurate delivery of radiation to the patient.

Thus, there exists a need for improved brachytherapy position verification systems and methods capable of confirming the placement of conduits within the patient, for detecting human error in transfer tube connection, and/or for promoting accurate radiotherapy source positioning. There also exists a need for a user- and patient-friendly position verification system and method that is effective, affordable, integrated into the work flow, and/or able to synchronize data between one or more of the various treatment planning, treatment delivery, imaging, and/or tracking devices.

SUMMARY

Embodiments of the present disclosure are directed to a position verification system.

In accordance with one embodiment, a treatment location verification system for confirming the position of a conduit inserted within a patient may include an elongate control element dimensioned for insertion within the conduit. The control element has a proximal end and a distal end, and a verification element coupled to a distal region. The verification element may be configured to detect the presence of a reference marker associated with the conduit and transmit a signal indicative of the position of the reference marker relative to the verification element. The system may also include a drive device coupled to a proximal region of the control element for controlling movement of the control element through the conduit, a controller configured to receive and process the signal transmitted by the verification element, and a signal conductor for transmitting the signal from the verification element to the controller.

Various embodiments of the disclosure may include one or more of the following aspects: at least one of the drive device and the controller may be included within an afterloader; the verification element may be further configured to emit a signal in order to detect the presence of the reference marker associated with the conduit; the control element may include a wire or a cable; the signal conductor may be further configured to transmit a signal from the controller to the verification element; the drive device may include a drum around which at least a portion of the control element is wrapped; the position verification system may include an electromagnetic transmitter, and the verification element may include at least one of a coil, a diode, an optical element, or a semiconductor component; the signal conductor may wirelessly communicate with the verification element and the controller; and the signal conductor may include an optical fiber, and the verification element may include at least one of a photo detector, a camera, an optical waveguide, a wavelength shifter, a scintillator, or a reflective surface.

In one embodiment of the present disclosure, a brachytherapy position verification system for confirming the position of a conduit inserted within a patient may include an elongate control element having a proximal end and a distal end and dimensioned for insertion within the conduit, and a verification element coupled to a distal region of the control element. The verification element may be configured to detect the presence of a reference marker associated with the conduit and transmit a signal indicative of the position of the reference marker relative to the verification element. The control element may be configured to maneuver the verification element along a length of the conduit. The system may also include an afterloader for delivering a radioactive treatment to the conduit. The afterloader may include a drive device for controlling movement of the control element through the conduit and a controller configured to communicate with the signal transmitted by the verification element. The system may further include a signal conductor for transmitting the signal from the verification element to the controller.

Various embodiments of the disclosure may include one or more of the following aspects: the controller may be configured to communicate with one or more of an imaging system, a treatment planning system, a treatment delivery system, and a tracking system; the controller may integrate the signal transmitted by the verification element with at least one of imaging data and electromagnetic tracking data; the verification element may include at least one of a semiconductor component, a diode, a coil, or an optical element; the controller may be configured to receive the signal from the verification element; the controller may be configured to transmit a signal to the verification element; and the afterloader may measure the distance that the verification element is inserted into the conduit.

In another embodiment of the present disclosure, a method of confirming the position of a conduit inserted in a patient may include inserting a verification element within the conduit, moving the verification element distally along a length of the conduit, and detecting a signal using the verification element, wherein the signal is indicative of the presence of a reference marker associated with the conduit. The method may further include transmitting the signal from the verification element to a controller and processing the signal to determine a position of the reference marker relative to the verification element.

Various embodiments of the disclosure may include one or more aspects: the method may further include transmitting data regarding the position of the reference marker to at least one of an imaging system, a treatment planning system, a treatment delivery system, and a tracking system; processing the signal may include synchronizing at least one of imaging data and electromagnetic tracking data with the signal transmitted by the verification element; the detecting, the transmitting, and the processing may be repeated as the verification element is moved distally along the length of the conduit; processing the signal may include determining whether the position of the reference marker relative to the verification element is within an expected predetermined distance threshold; the method may further include generating an error signal if the position of the reference marker relative to the verification element is outside of the expected predetermined distance threshold; and the method may further include automatically adjusting delivery of a treatment if the position of the reference marker relative to the verification element is outside of the expected predetermined distance threshold.

Additional objects and advantages of the embodiments will be set forth in part in the description that follows, and in part will be obvious from the description, or may be learned by practice of the embodiments. The objects and advantages of the embodiments will be realized and attained by means of the elements and combinations particularly pointed out in the appended claims.

It is to be understood that both the foregoing general description and the following detailed description are exemplary and explanatory only and are not restrictive of the claims.

BRIEF DESCRIPTION OF THE DRAWINGS

The accompanying drawings, which are incorporated in and constitute a part of this specification, illustrate the disclosed embodiments, and together with the description, serve to explain the principles of the disclosed embodiments. In the drawings:

FIG. 5A depicts a schematic view of exemplary components of a position verification system, according to an embodiment of the present disclosure;

FIG. 5B illustrates a schematic view of additional exemplary components of the position verification system of FIG. 5A, according to an embodiment of the present disclosure;

FIG. 6 illustrates a schematic view of components of an afterloader-integrated position verification system, according to an embodiment of the present disclosure;

FIG. 7A depicts a schematic view of the positioning of conduits and reference markers, according to an embodiment of the present disclosure;

FIG. 7B graphically depicts signals detected based on the reference marker locations depicted in FIG. 7A, according to an embodiment of the present disclosure;

FIG. 10 depicts a schematic view of an electromagnetic position verification system, according to an embodiment of the present disclosure;

FIG. 11A depicts a schematic view of the positioning of conduits relative to a target treatment area, according to an embodiment of the present disclosure;

FIG. 11B graphically depicts signals detected based on the target treatment area location depicted in FIG. 11A, according to an embodiment of the present disclosure;

DETAILED DESCRIPTION

Reference will now be made in detail to the exemplary embodiments of the present disclosure described below and illustrated in the accompanying drawings. Wherever possible, the same reference numbers will be used throughout the drawings to refer to same or like parts. For purposes of this disclosure, "proximal" refers to an end closer to the source of treatment (e.g., afterloader), and "distal" refers to an end further from the source of treatment. "Radiotherapy source" refers to a radioactive or x-ray source and encompasses both sources used for therapeutic and non-therapeutic purposes. "Communication" may refer to receiving signals, transmitting signals, or both receiving and transmitting signals. Additionally, the term "conduit" may refer to a catheter, needle, tube, applicator, applicator channel, or any suitable delivery pathway for a radiotherapy source.

While the present disclosure is described herein with reference to illustrative embodiments for particular applications, such as brachytherapy position verification systems for use with an afterloader, it should be understood that the embodiments described herein are not limited thereto. Those having ordinary skill in the art and access to the teachings provided herein will recognize additional modifications, applications, embodiments, and substitution of equivalents that all fall within the scope of the disclosed embodiments. For example, the principles described herein may be used with any suitable conduits (e.g., for use with injection needles, biopsy needles, catheters, applicators) for any suitable treatment or diagnostic purpose (e.g., brachytherapy, biopsies, or drug delivery), for any suitable part of the human anatomy (e.g., internal body cavities or superficial regions), and with either manual or automated delivery (e.g., with or without the assistance of a mechatronic device like an afterloader). Accordingly, the disclosed embodiments are not to be considered as limited by the foregoing or following descriptions.

Figure 1:
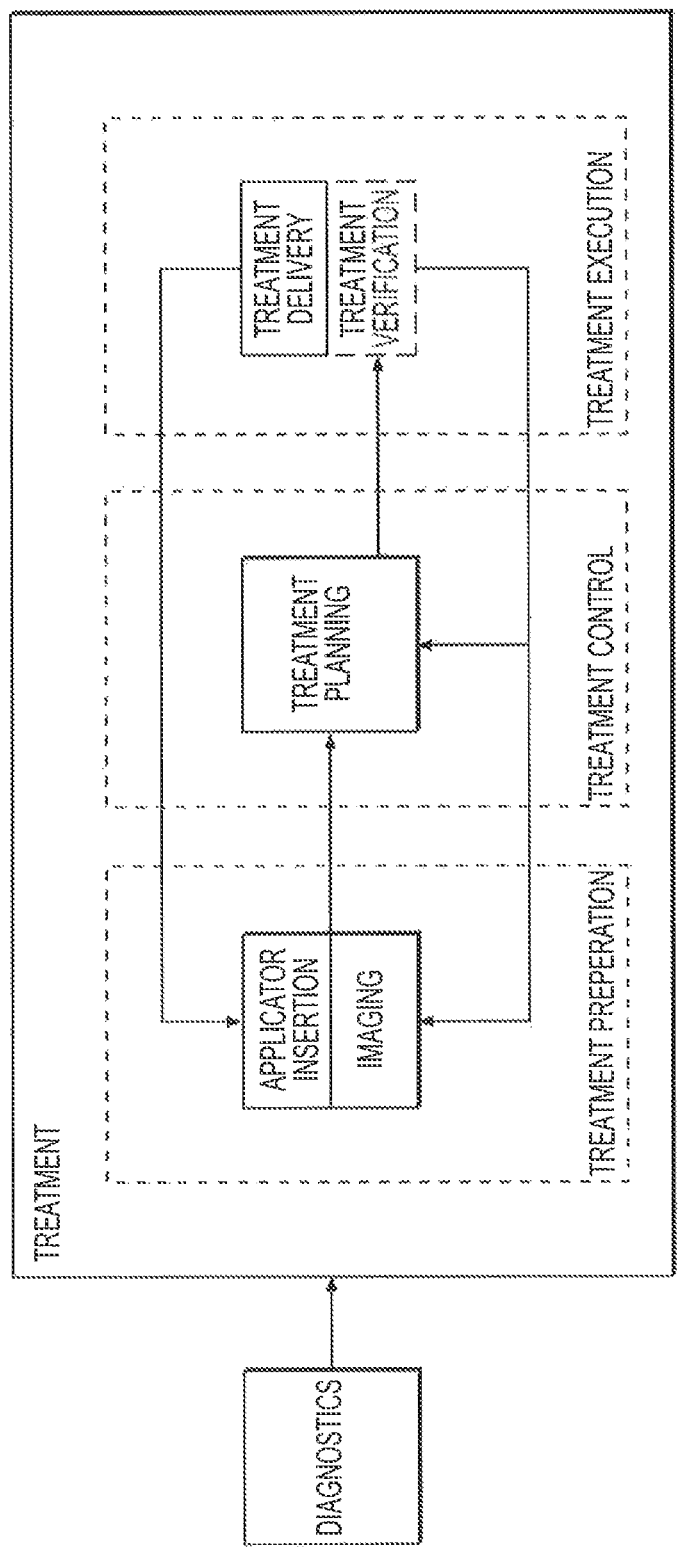
FIG. 1 illustrates an exemplary treatment workflow, according to an embodiment of the present disclosure.

Prior to providing a detailed description, the following overview is provided to generally describe the contemplated embodiments. In one embodiment, a position verification system may include a conduit having one or more reference markers located along the length of the conduit. Exemplary conduits include a transfer tube, a catheter, a needle, a tube, or an applicator, or a channel, catheter, tube, or needle within an applicator. As is shown in FIG. 1, brachytherapy treatment may include treatment preparation, control, and execution (e.g., one or more of applicator insertion with or without imaging, treatment planning, treatment delivery, with or without treatment verification). During treatment preparation, the conduit may be placed within a patient, and the reference markers associated with the conduit may be detected by a medical imaging system, such as magnetic resonance imaging (MRI), (computed) tomography (CT), (computed) radiography (CR), X-ray, elastography, thermography, photo acoustic imaging, tomography, angiography, optical, near infrared spectroscopy, electromagnetic, nuclear medical, and/or ultrasound imaging. The reference marker detection data may be transmitted to a processor for use with the planning treatment software and/or treatment delivery software. The treatment software analyzes this detection data and determines the two-dimensional or three-dimensional position of the reference marker (and thus conduit) within the patient.

During the treatment control stage, treatment planning may occur, and the precise dose distribution and dwell positioning may be mapped out, based on the positioning of the conduits relative to the patient anatomy. During treatment execution, treatment may be delivered via the conduits, and treatment verification may occur before, during, and/or after treatment delivery. Though the embodiment of FIG. 1 shows a clear, linear division, the steps may be rearranged or repeated as desired; for example, treatment control and/or execution may also include imaging, and treatment control and/or preparation may also include treatment verification.

Once in place, the verification element is then be passed into the one or more conduits, e.g., during the treatment control and/or treatment execution stage. The verification element may be configured to detect the reference markers to determine whether the positioning of the conduit is correct. The path of the verification element through the conduit may mimic the path that the radiotherapy source will take through the conduit, so use of the verification element to determine positioning relative to a reference marker may allow a healthcare provider to determine whether the radiotherapy source will be correctly positioned. Exemplary embodiments of this system are described in further detail below.

Figure 2:
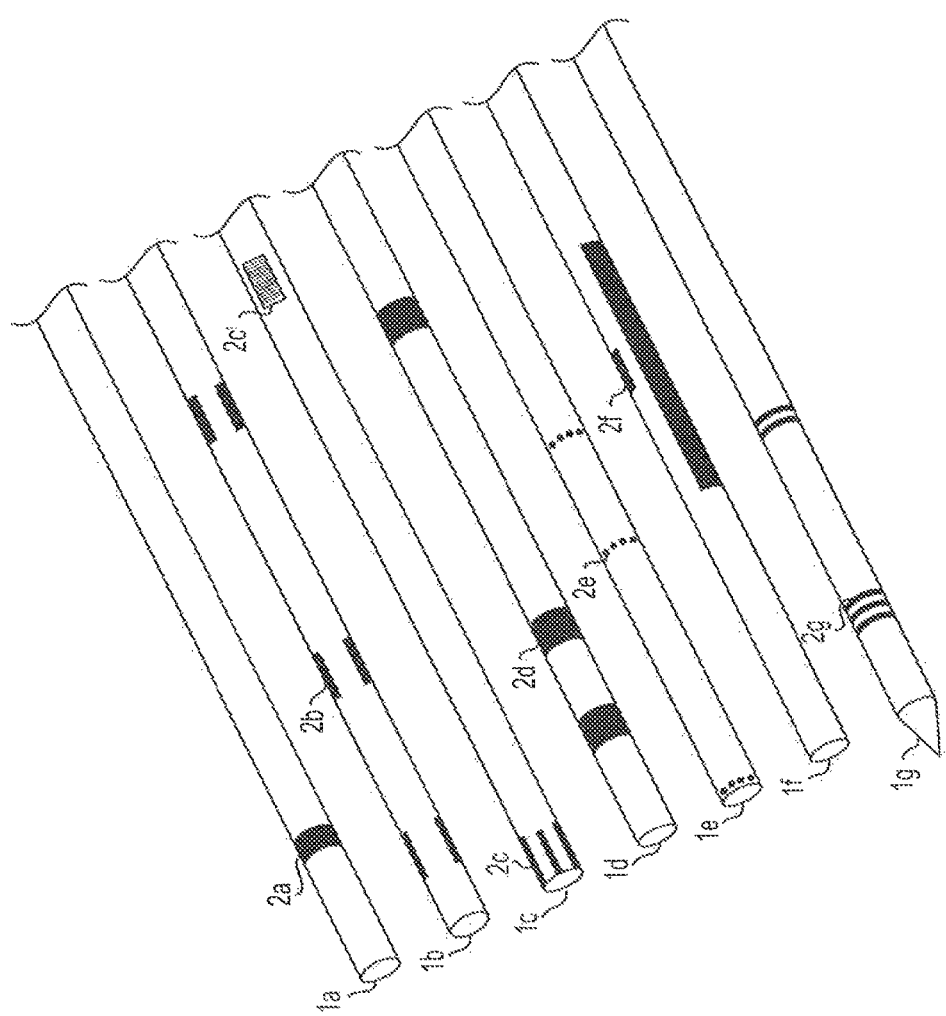
FIG. 2 illustrates a perspective view of exemplary reference markers, according to embodiments of the present disclosure.

As is shown in FIG. 2, conduits 1a-1g may include one or more reference markers 2a-2g along the length of the conduit. Reference markers 2a-2g may be located in any suitable position, e.g., within the walls of the conduit, on an outer surface of the conduit, on an inner surface of the conduit, may extend from an inner to an outer surface of the conduit, or any combination thereof. Reference markers 2a-2g may be located at any location of the conduit, along a side wall of the conduit, or multiple reference markers may be located in a combination of locations. The reference markers may be any suitable size, shape, or combination of sizes and/or shapes. For example, a reference marker may extend partially or entirely around the circumference of the conduit, either continuously (2a, 2d, 2g), or in a discrete pattern (2c, 2e). Multiple reference markers may be irregularly spaced along the length of the conduit (2e), or may be regularly spaced, or may be located on opposite sidewalls of the conduit (2b, 2f) or at set distances from one another. Additionally, the reference markers may be embedded within, lie flush with, protrude from, or be recessed within a sidewall of the conduit, or any combination thereof.

Figure 3A:
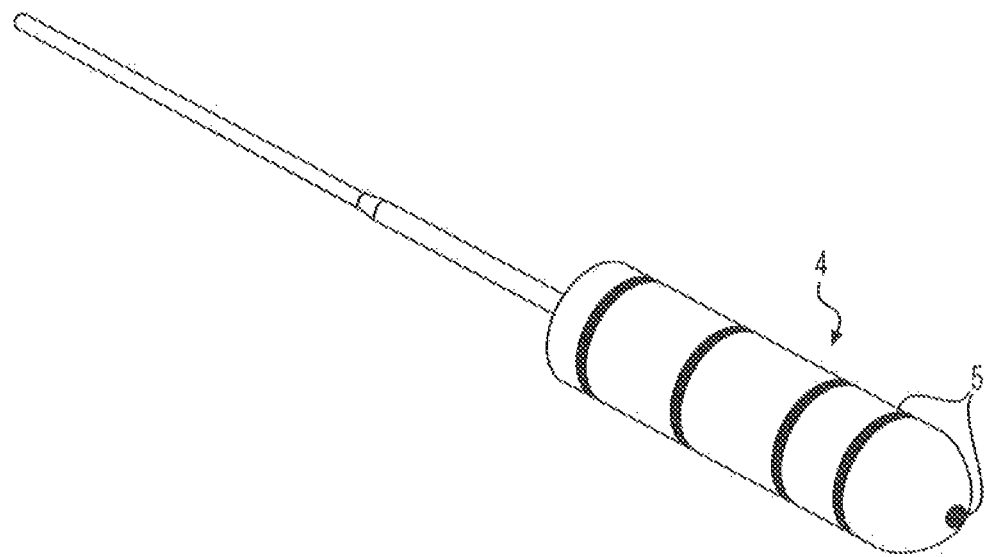
FIG. 3A illustrates a perspective view of an exemplary brachytherapy applicator, according to an embodiment of the present disclosure.
Figure 3B:
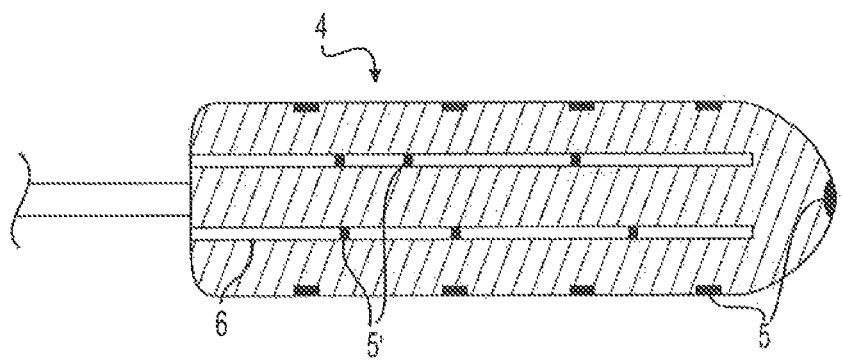
FIG. 3B depicts a cross-sectional view of the exemplary brachytherapy applicator of FIG. 3A, according to an embodiment of the present disclosure.

The reference markers may include, for example, rings, coils, magnets, biodegradable markers (e.g., polylactide markers detectable using fluorescence), printed patterns, radio-frequency identification (RFID) elements, openings in the conduit, and/or local areas of the conduit that are of a different physical configuration than the rest of the conduit (e.g., a different local material, geometry, or roughness), or any combination thereof. Exemplary reference markers may include, e.g., a printed code, such as a barcode (2c', 2g), a metallic ring or coil (2a), a radiopaque printed pattern (2e), or any suitable combination thereof. Reference markers may be formed of a suitable material or combination of materials, including, e.g., metal (e.g., a conductive, magnetic, or ferromagnetic metal), liquid, ink, plastic, ceramic, or glass. In embodiments in which the conduit is included in an applicator, as shown in FIGS. 3A and 3B, portions of an applicator 4 may include one or more reference markers 5. Additionally, one or more individual channel conduits 6 within applicator 4 may also include one or more reference markers 5'.

The one or more reference markers may be located in a predetermined location along the conduit. For example, the positioning of the reference markers may align with intended dwell positions of a radiotherapy source fed through the conduit, or may mark distance increments along the length of the conduit, or other pre-determined locations of the conduit, or may simply serve as a point of reference. For example, the larger reference marker in 2f may align with an area of interest, and the smaller reference marker in 2f may align with an intended dwell position along that target area. The different sizes or arrangements of reference markers may convey different types of information and may work best with different types of verification elements.

Further, the reference markers may be capable of being detected by one or more of a treatment delivery system, treatment planning system, tracking system, and/or imaging system. For example, an imaging system may be able to detect a metal ring, which may also be detectable by means of a coil inside the position verification element and by using an electromagnetic tracking device, as well as electronics incorporated into a treatment delivery system. Thus, detection of the reference markers in their respective locations may provide a way for the different positioning data to be synchronized and may facilitate communication between the various systems. The systems may also determine, assess, and/or adjust indirect measurements of the positioning of the reference marker and associated conduit within the patient. Such coordination and synchronization may promote the accuracy of treatment delivery and/or treatment planning.

Figure 4:
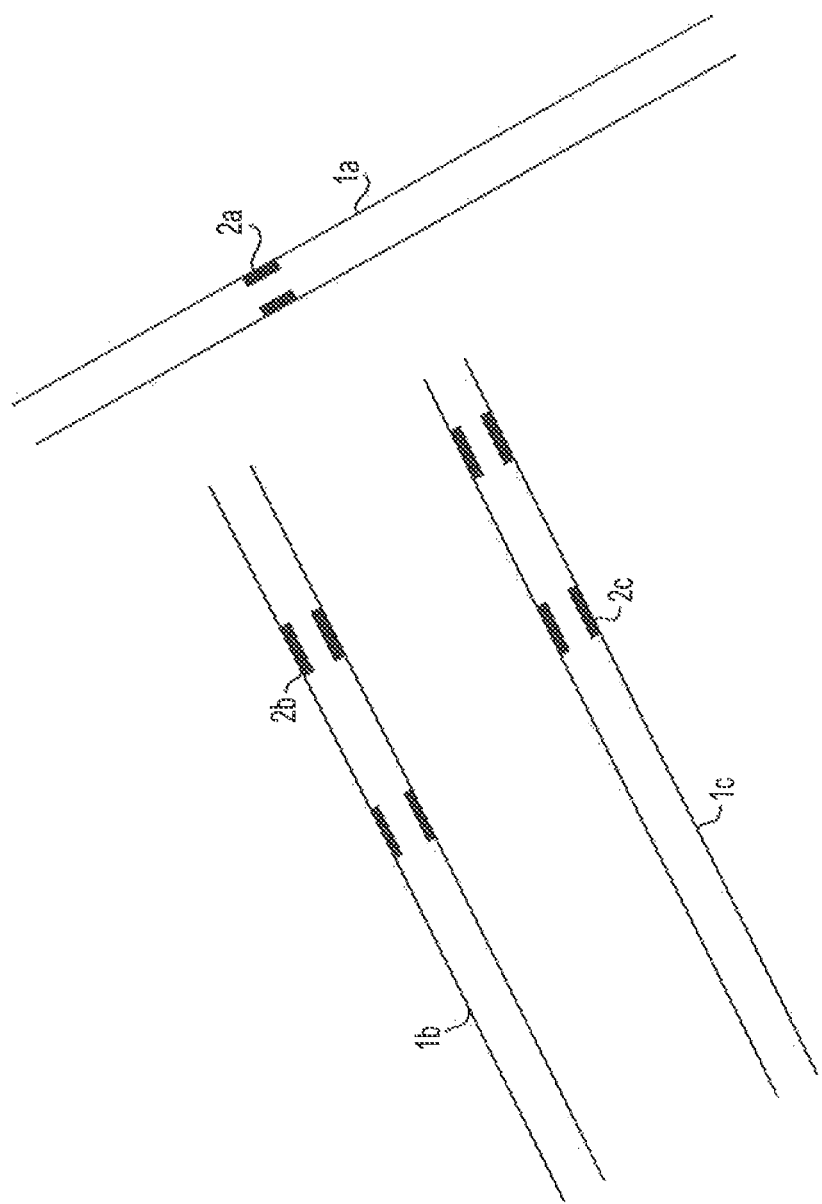
FIG. 4 depicts a schematic view of exemplary conduit positioning, according to an embodiment of the present disclosure.

As is shown in FIG. 4, multiple conduits may be spaced relative to each other at known locations. One or more conduits may include reference markers that align with or are placed near possible dwell positions, while one or more conduits may include reference markers that act as a reference for conduit or dwell positioning verification. In the embodiment of FIG. 4, conduits 1b and 1c include position reference markers 2b and 2c, respectively. Conduit 1a includes reference marker 2a, which acts as a point of reference for determining relative positioning of reference markers 2b and 2c. During conduit insertion, conduits 1a, 1b, and 1c are positioned in or near a target area and may be positioned in predetermined locations relative to each other. The reference markers of each conduit may be capable of being detected by treatment delivery, imaging, and/or tracking systems. Thus, the imaging system may determine the mutual position of the reference points, an afterloader may place a wire and/or verification element relative to the reference point to measure positioning, and a tracking (e.g., electromagnetic tracking) system may check the mutual position of the conduits. Any deviation of the relative distances and/or data, either within or between each system, may indicate shifting or movement of one or more conduits. Detection of the reference markers may provide a constant reference point with which to synchronize data across the systems. The systems may be separate from each other, may communicate with one another, or may be incorporated within a single system, e.g., a brachytherapy system with processing capabilities.

In embodiments in which multiple conduits are used in the treatment process, each conduit may have substantially uniform reference marker types and/or positions, or each conduit may have different reference marker types and/or different arrangements of reference markers. The differences in reference marker types and/or positions may indicate different information, e.g., different intended dwell positions and/or may aid in confirming the identity of each conduit to promote proper connection of the conduits to the brachytherapy system. For example, the position or type of a first reference marker in a conduit may identify the conduit, while the position or type of a second reference marker may be used to determine positional information. For example, a barcode, rings spaced in a certain pattern, or an RFID reference marker may identify the conduit, while a different type of reference marker or different amount of spacing may provide positional information. In conduit 1c of FIG. 2, barcode 2c' may identify the conduit, and reference markers 2c may provide positional information. In some embodiments, each conduit may include a type of reference marker that is different from the type used in other conduits, and the type of reference marker may identify the conduit, while the location of the reference marker may be used to provide positioning information.

The conduit may be formed of any suitable material, including, e.g., glass, plastic (with or without fillers, e.g., liquid silicone rubber, polyetheretherketone, polyphenylsulfone, polyethylene terephthalate, polycarbonate, polyimide, and/or polyoxymethylene), ceramic, metal (e.g., stainless steel, titanium, nitinol, tungsten) or metal alloys, composite material with fibers (e.g. epoxy, carbon, polybenzoxazole), or any suitable combination of materials. These materials may be biocompatible. The conduit may be rigid or flexible, or may have rigid and flexible portions. Further, the conduit may have any suitable cross-sectional shape and size, e.g., circular, rectangular, or oval cross-sectional shape, and may vary in size (e.g., length or width) depending on the desired amount, and/or rate of dosage to be delivered to a treatment site. In addition, one or more portions of the conduit may include a suitable shielding material to reduce radiation exposure of healthy tissue or organs. For example, stainless steel, titanium or tungsten, or alloys thereof, may be included in portions of the conduit to improve shielding.

The conduit includes a hollow inner portion dimensioned to receive a radiotherapy source or a verification element. After the conduit is positioned within a patient, the verification element may be passed through the hollow inner portion of the conduit from a proximal end to a distal region. This may occur during, before, or after the treatment planning stage, the treatment delivery stage, etc., or any combination thereof. To guide insertion and withdrawal, the verification element may be integrated in or coupled to a distal region of an elongate control element, e.g., a cable, a fiber, a foil, a tube, or a wire, which may be pulled and/or pushed proximally and distally to maneuver the verification element within the conduit.

The verification element may be configured to detect a reference marker (or vice versa) and/or may be configured to transmit a signal (e.g., optical or ultrasound pulses) to a receiving system, which may then be able to determine the position of the verification element. The verification element may detect or transmit, for example, an optical (e.g. ultraviolet, infrared) electrical, electromagnetic, magnetic, radiofrequency (RF), inductive, conductive, or capacitive signal. The verification element may be either passive (i.e., receive signals) or active (i.e., transmit signals or transmit and receive signals). In some embodiments in which the verification element is passive, the reference marker may itself be active and may include, e.g., a diode or other active signal. Thus, the verification element may be able to detect a reference marker as it approaches the location of the reference marker, or the verification element may be used to transmit a signal that may be detected by means of a receiving system located inside or outside of the patient or within the applicator. The verification element may be able to detect proximity to the reference marker and/or when the verification element has reached the location of the reference marker.

Exemplary verification elements may include one or more cameras, RFID devices, coils, antennas, diodes, optical fibers, magnets, capacitors, hall sensors, piëzo elements, photo detectors (e.g., photodiode, photomultiplier, charge-coupled device), light-emitting diodes, lasers, reflective surface, small microelectronic, microelectromechanical system (e.g., MEMS-device), semiconductor component, small electronic integrated circuit (IC), or small photonic integrated circuit (PIC), or any suitable combination thereof. Further, active verification elements and/or reference markers may include a source of electricity, e.g., a battery or a wired connection to an electrical source.

In the embodiment of FIG. 5A, a verification element 8 is located at a distal region of a cable 10. Verification element 8 is electrically coupled via a signal conductor 12 extending through or along cable 10 to a control system 14 coupled to a proximal end of cable 10. As is shown in FIG. 5B, verification element 8 and cable 10 are inserted into conduit 1. As verification element 8 passes a reference marker 2, verification element 8 detects the presence of reference marker 2. Verification element 8 then sends a signal depending on the reference marker to control system 14 via signal conductor 12. Signal conductor 12 may also relay signals to verification element 8. Additionally, verification element 8 may receive power from control system 14 via either signal conductor 12 and/or cable 10. For example, an active verification element 8 may receive power from control system 14 to power verification element 8 and/or transmit a signal, which may be reflected or altered by reference marker 2, and verification element 8 may detect this signal and transmit the signal to control system 14. In some embodiments, the verification element may receive power and/or a signal from the control system 14 that then allows it to transmit a signal that can be detected by a separate system. The separate system may then detect and process the signal of the verification element to determine the location of the verification element. Additionally, the separate system may detect an alteration in the signal caused by reference marker 2 so that the separate system can detect the location of reference marker 2 and verification element 8.

Signals may be relayed between verification element 8 and control system 14 on a continuous, temporary, or intermittent basis. If the signals are intermittently or temporarily transmitted, the timing may be at regular, spaced-apart intervals, or may be irregular, for example, increasing in frequency as the verification element approaches reference marker 2. In some embodiments, verification element 8 may be electrically coupled to control system 14 by a plurality of signal conductors 12. In other embodiments, verification element 8 may not be connected to any signal conductors and may instead wirelessly transmit information to control system 14, or to a separate system. Exemplary wireless embodiments may include, e.g., radio frequency (RF), telemetry (e.g., far-field radio-frequency or inductive telemetry), near field communication, magnetic field, Bluetooth, Zigbee, and/or infrared (IR) technology.

Control system 14 may include a processor 25 that interprets signals received and transmitted by verification element 8. Using at least the signals, processor 25 may determine the spatial positioning of verification element 8 relative to reference marker 2. In this way, processor 25 may determine whether or not the position of verification element 8, reference marker 2, and/or conduit 1 is correct, and thus whether the ultimate location of the radiotherapy source is correct. This processor may also be part of or may communicate with the treatment imaging, planning, tracking, and/or delivery systems to share, modify, merge, and/or compare this information.

Control system 14 may also include a drive system and/or accompanying electronics for controlling movement of cable 10 and verification element 8 through conduit 1, which may also be operably coupled to processor 25. Control system 14 may further include and/or communicate with a system equipped with a display panel or graphical user interface to display information about the detected signal, including positional information, to a user. Control system 14 may also include and/or communicate with a system equipped with a control panel to allow a user to input information, control the information being processed or displayed, control communication with other systems, or change the treatment delivery, for example.

Additionally, control system 14 may be part of a brachytherapy system (e.g., afterloader) or may be separate from a brachytherapy system. Inclusion within an afterloader may facilitate use of verification element 8 just prior to, during, or after treatment delivery. Control system 14 may include a power source, e.g., a replaceable or rechargeable battery and/or may be configured to connect to a source of power.

For example, as is shown in the embodiment of FIG. 6, drive system 15 may include a drum/wheel around which cable 10 is wound. Unwinding of the drum may be controlled by the control system or may be manually controlled. The drum may be operably coupled to a motor, crank, and/or any suitable automated or manual mechanism for winding and/or unwinding the drum. Drive system 15 may be part of an afterloader 16, which may control movement of verification element 8, in addition to delivery of one or more radiotherapy sources.

The systems may communicate with each other via communication standards, such as the DICOM-RT and/or dedicated software and hardware. For example, in operation, the reference marker data detected by the verification element may be compared to imaging information, including previously captured or real-time images of the conduit and reference markers within the patient. Images stored in one or more of the programs may be communicated and shared. Images of detected reference marker locations may be compared with the reference marker locations detected by the verification element. Accordingly, in some embodiments, the verification element may be used in conjunction with one or more external imaging devices.

In some embodiments, the verification element may be used separate from imaging devices, which may allow for position verification in environments in which imaging devices generally can't be used. This may include specially shielded rooms in which the patient undergoes radiation treatment. In some embodiments, the verification element data may be compared with measurement data collected by the afterloader, for example, measurements regarding the distance that the cable or verification element has been inserted into the conduit.

In FIG. 7A, three conduits (A, B, C), each with their own pattern of reference markers 2, are depicted. Though three conduits are depicted in FIG. 7A, any suitable number of conduits (e.g., one or a plurality) may be used. The number of conduits used in a given embodiment may be determined at least in part based on the target area location, target area size, patient anatomy, or disease state, for example. Conduits with reference markers 2 may be detected using a medical imaging system, as is depicted in FIG. 7A. One verification element may be passed through each of the three conduits one at a time, or multiple verification elements may be passed through the three conduits at the same time, with one verification element per conduit. One or more verification elements may be coupled to or integrated in one or more cables (e.g., in or onto a check cable, additional sensor cable, and/or a cable that also contains the radiotherapy source). As the verification element passes through each conduit and passes the location of a reference marker 2, the verification element detects a measurement value indicative of the presence of the reference marker. These measurement value signals may be communicated to the control system processor. Exemplary signal output values indicative of the presence of reference markers is graphically depicted in FIG. 7B. Changes (e.g., spikes and drops) in signal values as the verification element passes through the conduits may correlate with the position of the reference markers. Thus, the changes in measurement values detected by the verification element and transmitted to the control system processor correlate to the presence of a reference marker. Positioning of the reference markers, the conduits, and eventually the radiotherapy sources within the conduits, can be verified in this manner.

The position verification system may directly measure the reference marker location positions and/or conduit delivery path with the verification element and may verify whether the values of FIG. 7B match the image of FIG. 7A. Accordingly, the position verification system may be able to synchronize the location of the reference marker positions shown in FIG. 7A with the verification element data shown in FIG. 7B. The position verification system may also synchronize positional and/or imaging data from one or more of the diagnostic, planning, treatment, tracking, and/or delivery systems. For example, positioning may further be synchronized with measured values from an afterloader, such as the length of the verification element cable that has been inserted into the conduit.

If the position verification system detects a mismatch between the positioning detected by the verification element and the expected positioning location, the processor may send a signal indicating to the healthcare provider that something is wrong. This signal may be in the form of a visual and/or an audible signal, for example. Generating such a signal may promote the accuracy of treatment delivery by notifying a healthcare provider of a potential discrepancy prior to or during treatment delivery.

In some embodiments, when a deviation is detected, the system may not make any changes or generate any signal, for example, if the deviation is within a certain, predetermined threshold of tolerance. In this case, if position verification is being performed during treatment delivery, delivery may continue, or if position verification is being performed prior to treatment delivery, delivery may occur as planned.

If a deviation is detected that is outside a threshold level of tolerance, then the system may prevent or halt the delivery of radiotherapy treatment until after the discrepancy is corrected. The system may be configured to automatically fix the deviation (e.g., by adjusting or skipping dwell positions, or dwell times, or dosage), or the error may require manual fixing. In some embodiments, the detection of a deviation may result in a return to the treatment planning stage to adapt the plan to the current situation, or additional imaging may be taken to visibly assess the deviation, and, if required, adapt the treatment plan. Instead of, or in addition to, adjusting the plan, the conduits may be repositioned. If no deviations are detected, or if no deviations above a predetermined threshold level of tolerance are detected, treatment may be delivered and/or treatment delivery may continue. If a deviation is detected during post-treatment verification, future treatment plans or fractions may be altered. In this way, the verification system may promote more safe and accurate treatment delivery and may provide a convenient and more accurate method to verify if the radiotherapy source will be placed in the correct conduit and at the correct position in the conduit relative to the target area.

In some embodiments, the position verification system may also be able to detect a deviation between the expected conduit identity and the actual identity of the conduit in which the verification element is deployed. If a deviation is detected, the system may send a signal indicating to the healthcare provider that something is wrong. This may protect against human error, for example, in mixing up the transfer tube connections. In some embodiments, if the system detects that something is wrong, the system may prevent delivery of the radiotherapy source to the conduit until the discrepancy is corrected, and this correction may occur manually or automatically. The system may include one or more components and one or more processors in communication with the components and/or the other processors. For example, a processor may be included within or in communication with a computer, a detector, an afterloader, or any other suitable component of a brachytherapy system. Exemplary embodiments of position verification systems are explained in further detail below.

In some embodiments, the verification element may be able to send a signal, which the reference marker may reflect, and this reflected signal may be detected by the verification element. In some embodiments, the reference marker may be able to send a signal, which the verification element may reflect, and this reflected signal may be detected by the reference marker. In still other embodiments, the verification element may send a signal, which the reference marker may receive. The reference marker may then send information regarding the received signal to a controller. And, in other embodiments, the reference marker may send a signal, which the verification element may receive. The verification element may then send information regarding the received signal to a controller, e.g., via the signal conductor.

Figure 8:
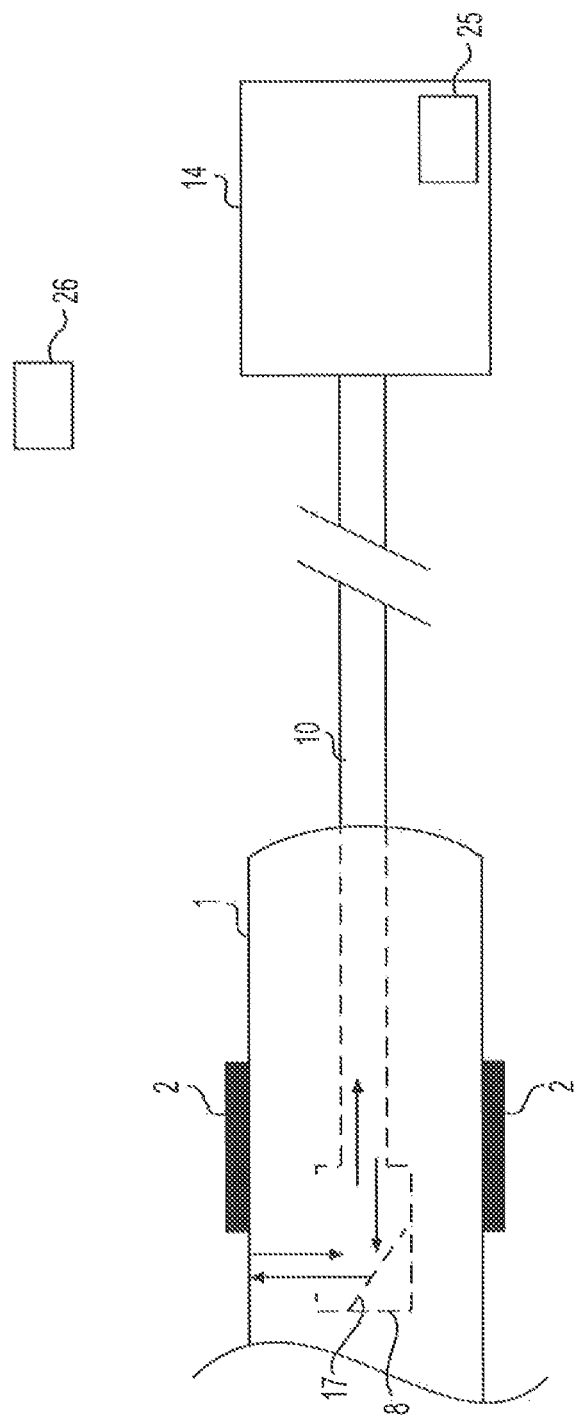
FIG. 8 depicts a schematic view of an exemplary optical position verification system, according to an embodiment of the present disclosure.

In an exemplary optical embodiment, the verification element may be configured to detect a comparative difference in an optical property between the conduit and the reference marker, or vice versa. For example, the amplitude, phase/delay, frequency/wavelength, refraction, interference, or other signal property or combination of properties could be detected by either the verification element or the reference marker. In the embodiment of FIG. 8, optical verification element 8 may detect a change in light reflection as it approaches, reaches, or passes reference marker 2 of conduit 1. Optical verification element 8 may include, for example, one or more of a photo detector (e.g., photodiode, photomultiplier, charge-coupled device), a camera, a laser, an optical fiber, an optical waveguide, a reflective surface, a lens, a prism, a filter, a beam splitter, a polarizer, grating, or any suitable combination thereof. Suitable reference markers for use with an optical verification element may include, for example, a radiopaque marker (e.g., a radiopaque marker and/or a printed ink), a locally different material (e.g., a locally darker or lighter and/or more or less dense material), or a locally more or less reflective material (e.g., a metallic and/or polished surface). In an exemplary embodiment, a radiopaque ink may be printed on a surface of a plastic conduit. Further, if verification element 8 is passive, reference marker 2 may emit light and may include, for example, fluorescence material or light emitting fibers or diodes.

In optical embodiments, a signal conductor may include, for example, one or more electrical cables or wires, or one or more optical fibers, or a combination thereof. The signal conductor may power either the reference marker or the verification element or may be used for transmitting signals. In some embodiments, the reference marker may be able to use the signal energy (e.g., light or electromagnetic energy) from the verification element for powering. The signal conductor may connect the verification element and/or the reference marker with control system 14 and may be located within the walls of the conduit, external to the conduit, or within the conduit. In some embodiments, signals may be transmitted wirelessly between verification element 8 and control system 14 or another system 26.

In the embodiment of FIG. 8, an optical fiber may transmit light from control system 14 to verification element 8, and a reflective surface 17 (e.g., a mirror and/or other optical elements) may direct, magnify, and/or or focus the light onto a surface (e.g., wall) of conduit 1. The wall of conduit 1 may reflect light back to reflective surface 17 and cable 10 may transmit the reflected data through the optical fiber to control system 14, which may contain hard-wired, wireless charged, or battery-operated electronics and optical elements for emitting and detecting light (e.g., one or more lamps, LEDs, lasers, photo detectors, diodes, photomultipliers, lenses, filters), and associated processor 25. The system may determine a characteristic of the reflected light, for example the frequency, intensity, angle of incidence, or spectrum. When verification element 8 approaches, reaches, or passes reference marker 2, the characteristic of the reflected light changes, and processor 25 may calculate the positioning of verification element 8 relative to reference marker 2 based at least in part on this change.

Figure 9A:
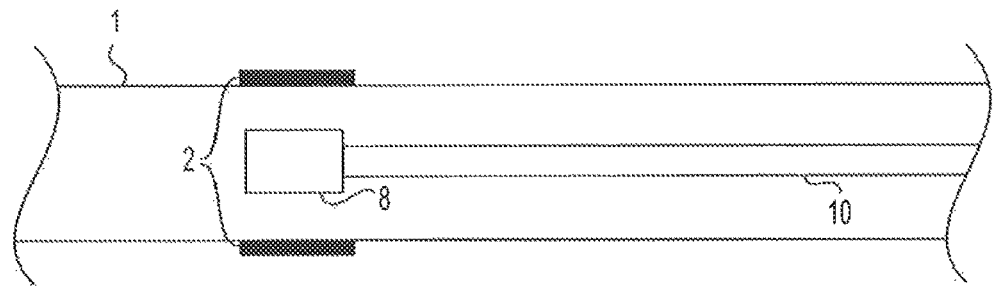
FIG. 9A illustrates a schematic view of an electromagnetic position verification system, according to an embodiment of the present disclosure.
Figure 9B:
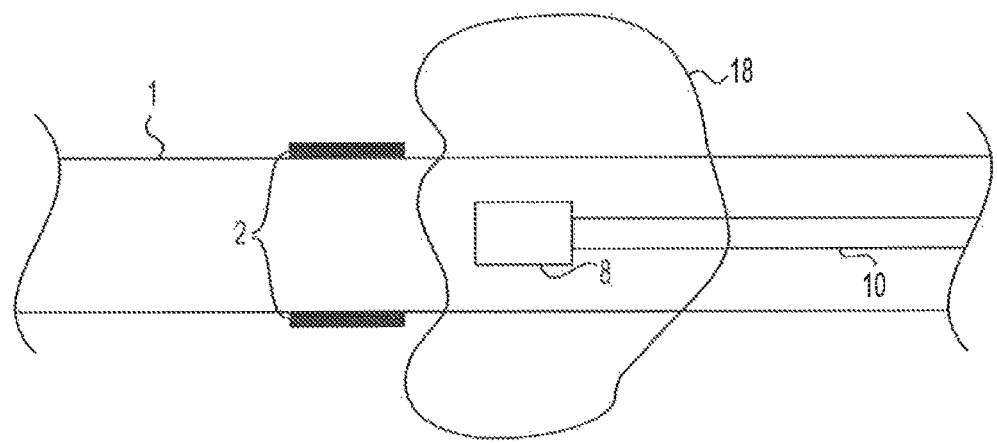
FIG. 9B illustrates a schematic view of an electromagnetic position verification system with an active verification element, according to an embodiment of the present disclosure.
Figure 9C:
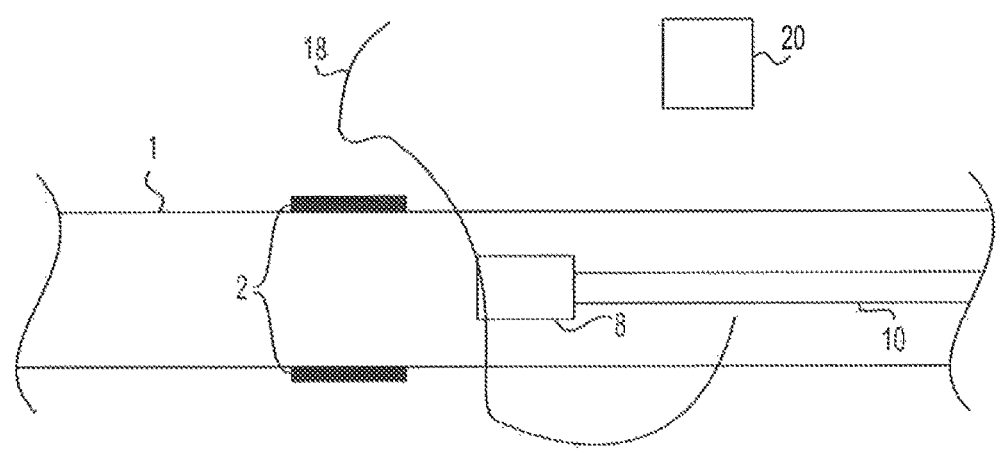
FIG. 9C illustrates a schematic view of an electromagnetic position verification system with a passive verification element, according to an embodiment of the present disclosure.

In the embodiments of FIGS. 9A-9C, electromagnetic position verification systems are depicted. Verification element 8 may be either active or passive. In an active embodiment, as shown in FIG. 9B, verification element 8 may generate an electromagnetic field 18 and detect a deviation in the signal that is indicative of a reference marker 2 as it approaches, reaches, or passes reference marker 2. In an exemplary active embodiment, a conductive reference marker may form a ring around the circumference of the conduit, or a plurality of reference markers may be located across from one another on the opposite walls of the conduit. The active verification element 8 may generate an electromagnetic field 18 and detect a signal change caused by the conductive reference markers as it approaches, reaches, or passes through the reference markers. A passive verification element may not generate an electromagnetic field and may instead only detect a signal. In the embodiment of FIG. 9C, a separate electromagnetic transmitter 20 may generate an electromagnetic field, and verification element 8 may detect a change in one or more signal characteristics when it approaches, reaches, or passes by a reference marker 2. In some embodiments, the verification element may be able to switch between an active mode and a passive mode.

The position verification system of FIG. 10 includes an electromagnetic transmitter 20 for generating an electromagnetic field to be detected by verification element 8. The signal detected by verification element 8 may then be transferred by signal conductor 12 to a processor and/or drive electronics. An exemplary electromagnetic tracking system is the Aurora® Electromagnetic Measurement System of NDI. Verification element 8 may include one or more coils, e.g., induction coils, and the switching magnetic field may induce changing currents in the coil that allow the 3D position of the coil to be detected. These signals received by verification element 8 may be transmitted to the control system either wirelessly or via a signal conductor 12 and may be interpreted by the control system processor. For example, a metallic reference marker, e.g., a ferromagnetic or conductive reference marker, may cause a local disturbance in the electromagnetic field, and this disturbance may be detected as verification element 8 approaches, reaches, and/or passes by this reference marker.

The control system may include (drive) electronics with a switching unit 21. In a first position, depicted in FIG. 10, switching unit 21 may connect verification element 8 with the electronics of the electromagnetic tracking system to determine the 3D position of the verification element (i.e., by completing the circuit between point X and point Y). In a second position, verification element 8 may be connected with the reference marker detection electronics when switching unit 21 completes the circuit between point X and point Z. The switching unit may switch between the two or more positions, optionally connecting the verification element with either the electromagnetic tracking system or the reference marker detection electronics. The switching may occur at any suitable rate, and the rate of switching may be regular or irregular. Further, the rate of switching may be manually controlled by a user or may be automatically controlled by control system 14. This switching configuration may integrate an electromagnetic tracking system with the position verification system and allow the reference markers, the electromagnetic tracking data, and the dwell positions of the verification element to be merged and/or synchronized into a single two-dimensional or three-dimensional spatial positioning database. When the reference marker locations are also known in images (either real-time or stored images), these images may also be merged/synchronized to the same two-dimensional or three-dimensional coordinates. To merge three-dimensional data, at least three reference points may be required, while two-dimensional tracking may require fewer coordinates. The electromagnetic tracking system may include a sensor with multiple Degrees-Of-Freedom, e.g., 3DOF or more, and exemplary systems may use two, three, or more reference points.

In some embodiments, the function of the verification element and the reference markers may be inverted. For example, the verification element may emit/transmit signals, and the reference markers included in the conduit may receive those signals. The reference markers may communicate with the control system (either wirelessly or via one or more signal conductors) and may transmit information about the received signal. Thus, the reference markers may detect the approach of an emitted signal, instead of vice-versa, and the reference marker positioning may be verified in this manner.

Further, in some embodiments, a single verification element cable may include multiple verification elements. This configuration may provide redundancy, which may promote more accurate verification. In some embodiments, different sensors on a single cable may respond to different reference marker types included in the conduit. For example, if a single conduit includes a plurality of different reference markers (e.g., barcode, coding, or RFID conduit identification marker and separate positional reference marker), a single cable with multiple verification elements may be able to detect information from both types of reference markers. In such embodiments, each verification element may be connected to its own signal conductor, each verification element may share a signal conductor, each sensor may be wireless, or any suitable combination thereof.

In some embodiments, tissue of the patient may itself be used as a reference marker, and a verification element and conduit may be configured to directly detect this tissue. Either healthy or diseased tissue may be used as a reference. For example, a diseased portion of the tissue may have different reflective properties, may sit in a specific relative location, or may lie in a different plane. Likewise, a different portion of healthy tissue may have different reflective properties, may sit in a specific relative location, or may lie in a different plane.

In the embodiment of FIGS. 11A and 11B, a transparent conduit 1 may be inserted into a patient's body in or near a tissue (e.g., Target Volume) area 23. As is shown in FIG. 11A, an optical verification element 8 may be inserted into conduit 1. Verification element 8 may be configured to emit and/or detect light. Tissue area 23 may reflect light differently than the surrounding area and/or tissue, and when verification element 8 approaches, reaches, and/or passes by tissue (or target treatment) area 23 in transparent conduit 1, verification element 8 may detect a change in the reflected light that is indicative of tissue area 23.

FIG. 11B shows an exemplary graphical depiction of the sensed optical data. As verification element 8 approaches a region of conduit 1 adjacent tissue area 23 (designated with symbol '*'), a property of the reflected light detected by verification element 8 may change, as is shown in FIG. 11B. This change may remain steady, may decrease, or may increase as verification element 8 passes tissue area 23 until verification element 8 begins to move past tissue area 23. When verification element 8 moves out of range of tissue area 23 (designated with symbol '#'), the property of reflected light may return to baseline measurements. This change in detected light property may be gradual (as is shown in FIG. 11B), or may occur more abruptly, for example, depending on the light property measured, the sensitivity of verification element 8, the transparency of conduit 1, patient anatomy, and/or the local properties around the conduit.

It is also possible to use the verification element to detect the tissue around the conduit before, during, and/or after treatment delivery to verify any deviations (e.g., shifts of conduits related to tissue and/or tissue responses caused by radiation treatment).

Figure 12A:
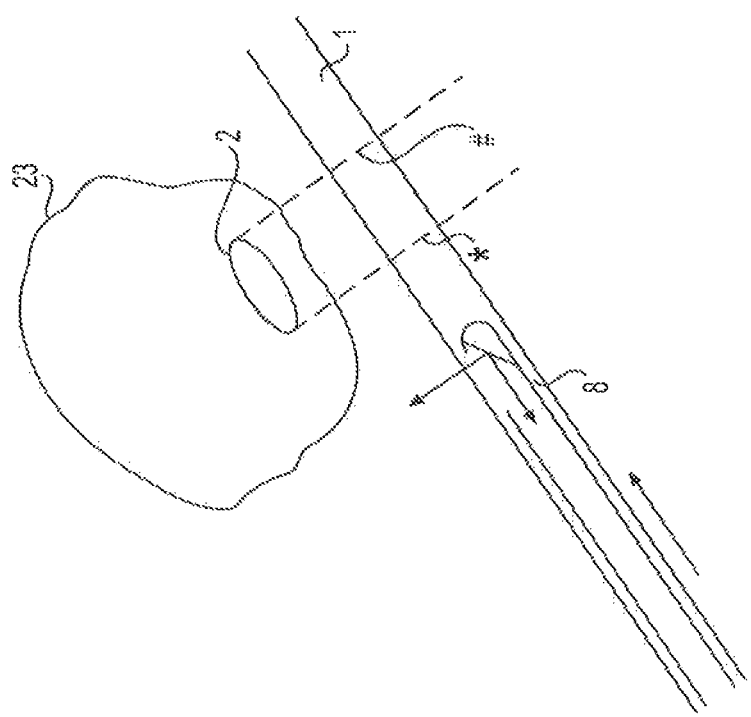
FIG. 12A depicts a schematic view of the positioning conduits relative to a marker located in a target treatment area, according to an embodiment of the present disclosure.
Figure 12B:
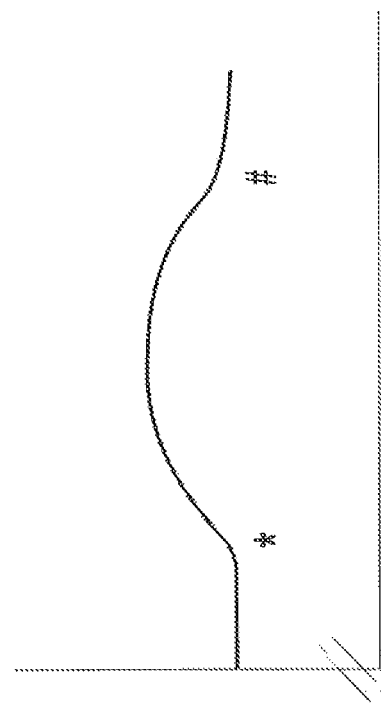
FIG. 12B graphically depicts signals detected based on the marker location depicted in FIG. 12A, according to an embodiment of the present disclosure.

In some embodiments, one or more reference markers 2 may be placed directly in or around a target tissue area (e.g., in or near an organ at risk, in a body cavity, on the skin of the patient, or in/at a tissue or body support like a patient table), rather than being associated with a conduit, as shown in FIGS. 12A and 12B. The tissue of the patient may be marked by applying or embedding substances with physical properties that are different than those of the surrounding environment. For example, one or more liquids or solutions may be injected into or painted onto the tissue, or one or more permanent or temporary solid markers may be implanted into or onto the tissue. Exemplary markers may include fluorosensors, fluorescent dyes such as indocyanine green, biodegradable markers, and/or (bio)medical tracers that bind to cancerous tissue or react to (gamma) radiation applied during treatment delivery or verification.

Similar to the process described above in reference to FIGS. 11A and 11B, in FIGS. 12A and 12B, a conduit 1 may be inserted into a patient's body in or near a tissue 23 (e.g., Target Volume) area that has been marked with reference marker 2. An optical verification element 8 may be inserted into conduit 1. The conduit may be optically transparent (e.g., if an optical signal is used) and/or may be formed of a material that allows a signal to pass through the conduit in order to pass between verification element 8 and reference marker 2. Verification element 8 may be configured to emit and/or detect light, and tissue marker 2 may reflect light differently than the surrounding area and/or tissue. When verification element 8 approaches, reaches, and/or passes by the area of reference marker 2 associated with the tissue, the verification element may detect a change in the reflected light that is indicative of tissue marker 2.

FIG. 12B shows an exemplary graphical depiction of the sensed reference marker 2 associated with the tissue. As verification element 8 approaches a region of conduit 1 adjacent reference marker 2 associated with tissue area 23 (designated with symbol '*'), a property of the reflected light detected by verification element 8 may change, as is shown in FIG. 12B. This change may remain steady, may decrease, or may increase as verification element 8 passes reference marker 2 associated with tissue area 23 until verification element 8 begins to move past reference marker 2. When verification element 8 moves out of range of reference marker 2 (designated with symbol '#'), the property of reflected light may return to baseline measurements. This change in detected light property may be gradual (as is shown in FIG. 12B), or may occur more abruptly, for example, depending on the light property measured, the sensitivity of verification element 8, the transparency of conduit 1, patient anatomy, and/or the local properties around the conduit. As will be recognized by one of skill in the art, the property changes of other, non-optical signal types may also be used to detect reference marker 2.

Though optical embodiments are described in the above examples, any suitable signals, reference markers, and verification elements may be used, so long as the signal type is compatible with the type of tissue marker implanted may be used. For example, electromagnetic or ultrasound signals may be used, and the reference markers may interact with the signals to cause a detectable change. In an exemplary ultrasound embodiment, verification element 8 may emit sound waves, and reference marker 2 may cause changes in the sound waves that may then be detected, e.g., by verification element 8 or a separate system.

Figure 13:
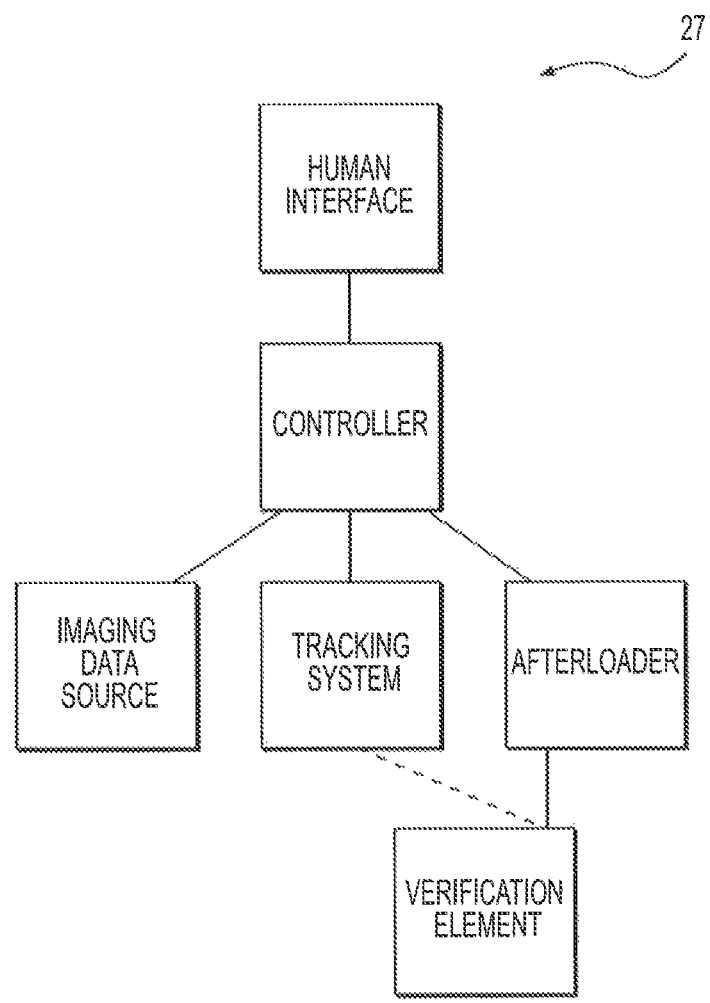
FIG. 13 depicts a block diagram shown an exemplary workflow interface, according to a further embodiment of the present disclosure.
Figure 14:
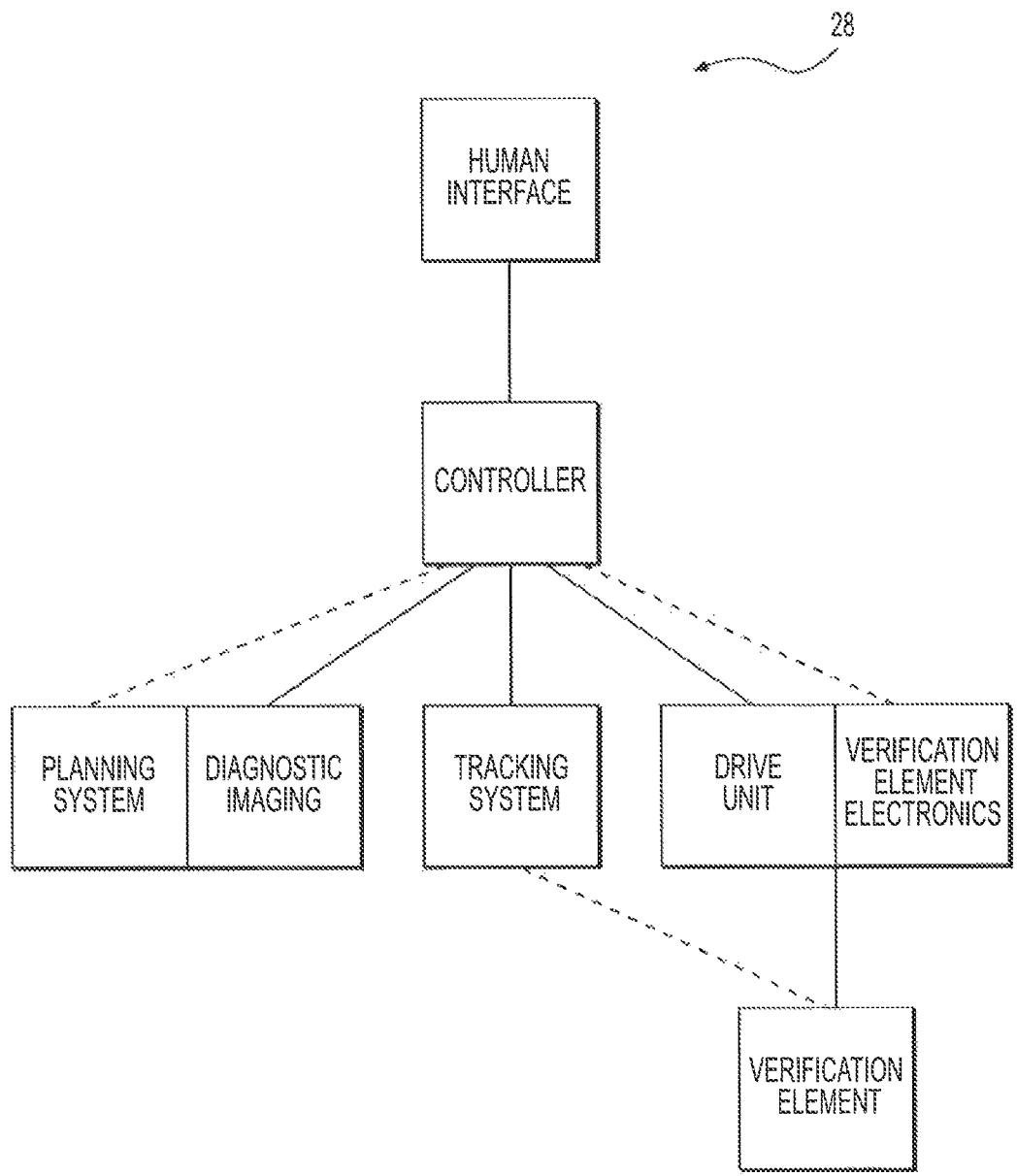
FIG. 14 depicts a block diagram shown an exemplary workflow interface, according to a further embodiment of the present disclosure.
Figure 15:
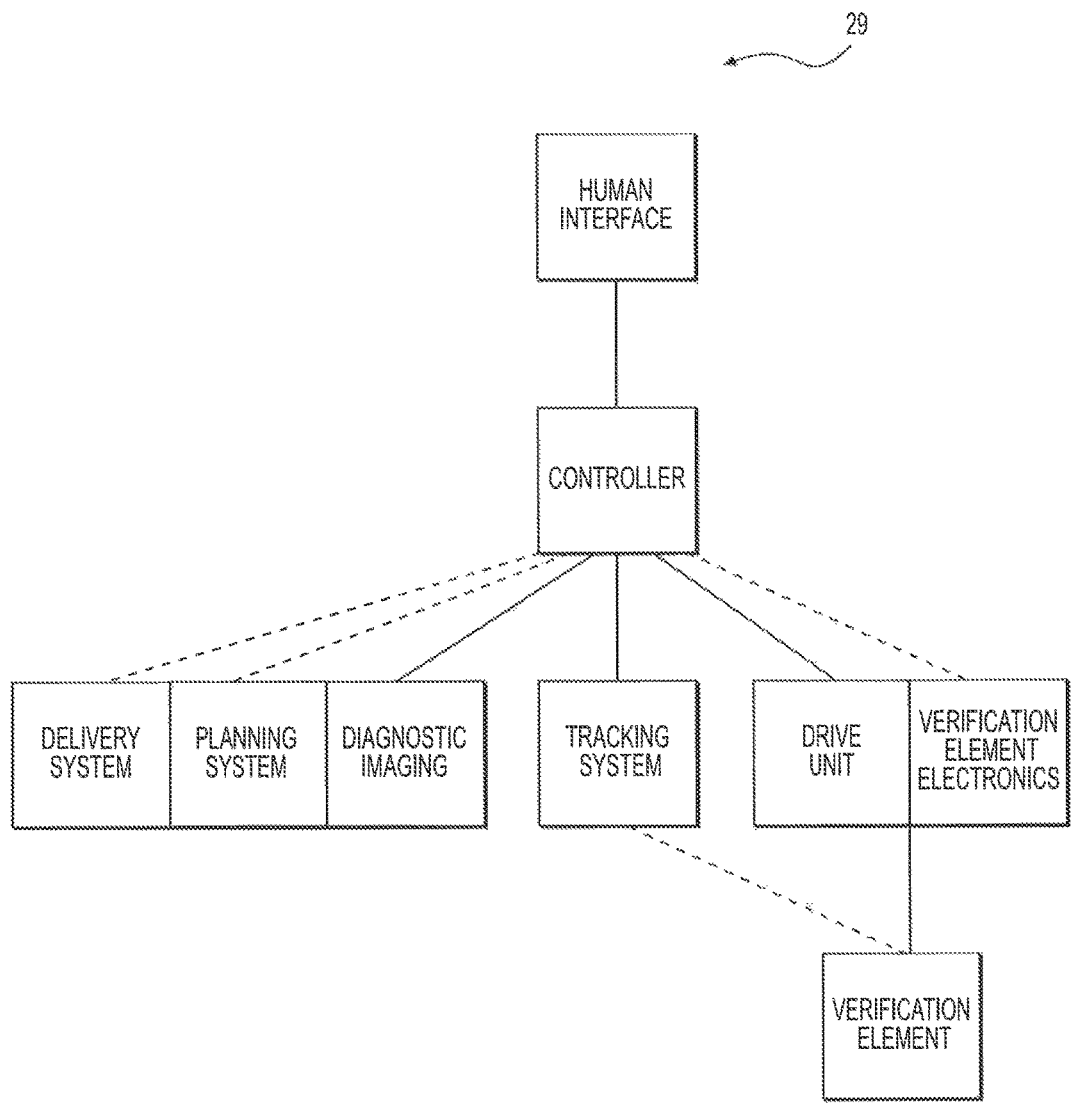
FIG. 15 depicts a block diagram shown an exemplary workflow interface, according to a further embodiment of the present disclosure.

FIGS. 13, 14, and 15 provide an overview of exemplary brachytherapy systems that use a verification element to detect the location of conduits that will be used to deliver treatment in order to promote more accurate dose delivery. In the embodiment of FIG. 13, the verification element communicates with an afterloader regarding the detected position of one or more reference markers, which may be used to determine the location of one or more conduits. A tracking system may also communicate with the verification element in order to determine the location of the reference marker(s). Based on this information, system 27 may determine whether the conduits are located in the intended location, or, if there is a deviation from the intended location, whether the actual location is within an acceptable threshold of deviation. To help in this determination, the controller may communicate with an imaging data source to compare the detected location of the conduits with an image of the conduits within the body or to compare the detected location of the conduits with an image of the surrounding body structures. The image may have been taken at an earlier step, e.g., during treatment preparation or planning, or may be taken during the verification procedure. A controller may act as the interface between the various components of system 27, controlling communications between the components and/or controlling the actions of one component based on signals received from that component, another component, or based on data received from multiple components.

As is shown in FIG. 14, a system 28 may include a drive unit and verification element electronics for controlling movement of the verification element relative to the conduits and/or reference markers. These components may be independent from an afterloader device, or may be included in an afterloader device, and may work with a tracking system to determine the location of the verification element relative to the reference marker(s). All three components may be in communication with the verification element, and the controller may adjust the drive unit or the electronics based on information gleaned from the verification element, the tracking system, the drive unit, or the verification element electronics. Based on this information, system 28 may determine whether the conduits are located in the intended location, or; if there is a deviation from the intended location, whether the actual location is within an acceptable threshold of deviation. To help in this determination, the controller may communicate with an imaging data source, as describe in system 27 of FIG. 13. Further, the controller may communicate with a planning system to further determine whether the intended dose distribution will be achieved within an acceptable threshold based on the actual location of the reference markers and conduits that is detected by the verification element. Additionally, as is shown in system 29 of FIG. 15, the controller may also communicate with a delivery system to adjust the actual delivery of treatment, if desired, based on the actual location information detected.

Although a hierarchical relationship is shown in the exemplary figures, any component may interact directly with any other component, or, as is show, one or more of the components may be routed through a controller. Additionally, one or more components may be housed within the same structure, e.g., an afterloader, or the components may be located separate from each other or even remote from each other, and the components may be connected to each other wirelessly, through hard wired connections, or a combination of the two. For example, a remote computer database may wirelessly communicate with and control the other components, or the controller may be included within an afterloader device. Further, control of the components may be automatic, based on pre-programmed input and feedback from the components, or control of the components may be manual, e.g., through user input. Even if the components are automatically controlled, a user may be able to alter or override the automatic adjustments.

The many features and advantages of the present disclosure are apparent from the detailed specification, and thus, it is intended by the appended claims to cover all such features and advantages of the present disclosure that fall within the true spirit and scope of the present disclosure. Further, since numerous modifications and variations will readily occur to those skilled in the art, it is not desired to limit the present disclosure to the exact construction and operation illustrated and described, and accordingly, all suitable modifications and equivalents may be resorted to, falling within the scope of the present disclosure.

Moreover, those skilled in the art will appreciate that the conception upon which this disclosure is based may readily be used as a basis for designing other structures, methods, and systems for carrying out the several purposes of the present disclosure. Accordingly, the claims are not to be considered as limited by the foregoing description.

What is claimed is:

1. A brachytherapy verification system for confirming the position of a conduit inserted within a patient, comprising:
   a control element dimensioned for insertion within the conduit, wherein the control element has a proximal end and a distal end;
   a verification element coupled to a distal region of the control element, wherein the verification element is configured to detect the presence of a reference marker associated with the conduit and communicate a signal indicative of the position of the reference marker relative to the verification element, and wherein the control element is configured to maneuver the verification element along a length of the conduit;
   a drive system coupled to a proximal region of the control element for controlling movement of the control element through the conduit;
   a controller associated with the verification element, wherein the controller is configured to communicate with the verification element;
   a signal conductor to conduct the signal between the verification element and the controller; and
   a brachytherapy afterloader, wherein at least one of the drive system or the controller is a component of the afterloader.

2. The brachytherapy verification system of claim 1, wherein the reference marker is further detectable by at least one of an imaging system, a treatment delivery system, or a tracking system when the reference marker is inserted within the patient.

3. The brachytherapy verification system of claim 2, wherein the tracking system is an optical tracking system.

4. The brachytherapy verification system of claim 2, wherein the imaging system includes at least one of a radiography, an X-ray, an MRI, or an ultrasound system.

5. The brachytherapy verification system of claim 1, wherein the verification element is further configured to emit a signal in order to detect the presence of the reference marker associated with the conduit.

6. The brachytherapy radiotherapy verification system of claim 1, wherein the control element includes a wire or a cable.

7. The brachytherapy verification system of claim 1, wherein the signal conductor is further configured to transmit a signal from the controller to the verification element.

8. The brachytherapy verification system of claim 1, wherein the drive system includes a drum around which at least a portion of the control element is wrapped.

9. The brachytherapy verification system of claim 1, further comprising an electromagnetic transmitter for generating an electromagnetic field, wherein the verification element includes a coil, and wherein the verification element is configured to detect a change in the generated electromagnetic field that correlates to the position of the reference marker relative to the verification element.

10. The brachytherapy verification system of claim 1, wherein the signal conductor is at least one of a cable, a wire, or a wireless connection between the verification element and the controller.

11. The brachytherapy verification system of claim 1, wherein the signal conductor includes an optical fiber for conducting light between the verification element and the controller and wherein the verification element includes at least one of a photo detector, a camera, an optical waveguide, a wavelength shifter, a scintillator, or a reflective surface.

12. The brachytherapy verification system of claim 1, wherein the verification element includes a light-emitting diode, the reference marker includes a material having a different reflective property than a reflective property of the conduit, and the verification element is configured to detect a change in the reflective property indicative of the reference marker.

13. The brachytherapy verification system of claim 1, wherein the verification element is configured for insertion within the conduit and is configured to move distally along the length of the conduit; and wherein the brachytherapy verification system is configured to determine the position of the reference marker relative to the verification element and whether the position of the reference marker relative to the verification element is within an expected predetermined distance threshold.

14. The brachytherapy verification system of claim 1, wherein the brachytherapy verification system is further configured to transmit data regarding the position of the reference marker to at least one of an imaging system, a treatment planning system, a treatment delivery system, or a tracking system.

15. The brachytherapy verification system of claim 1, wherein the controller is configured to synchronize imaging data received from an imaging system with the signal communicated by the verification element.

16. The brachytherapy verification system of claim 1, wherein the brachytherapy verification system is further configured to detect, transmit, and process the signal, and to repeat the detecting, the transmitting, and the processing of the signal as the verification element is moved distally along the length of the conduit.

17. The brachytherapy radiotherapy verification system of claim 1, wherein the controller is configured to generate an error signal if the position of the reference marker relative to the verification element is outside of an expected predetermined distance threshold.

18. The brachytherapy verification system of claim 1, wherein the controller is configured to automatically adjust delivery of a treatment if the position of the reference marker relative to the verification element is outside of an expected predetermined distance threshold.

19. The brachytherapy verification system of claim 1, wherein the conduit is a first conduit and the reference marker is a first reference marker, and wherein the controller is configured to determine whether a position of the first reference marker relative to a position of a second reference marker is outside of an expected predetermined distance threshold, wherein the second reference marker is associated with the first conduit or a second conduit.

20. The brachytherapy verification system of claim 1, wherein the controller is configured to measure a distance that the verification element has been inserted into the conduit.

21. A brachytherapy verification system for confirming the position of a conduit inserted within a patient, comprising:
   a control element dimensioned for insertion within the conduit, wherein the control element has a proximal end and a distal end;
   a verification element coupled to a distal region of the control element, wherein the verification element is configured to detect the presence of a reference marker associated with the conduit and transmit a signal indicative of the position of the reference marker relative to the verification element, and wherein the control element is configured to maneuver the verification element along a length of the conduit;

a brachytherapy afterloader for transferring a radiotherapy source inside the conduit, wherein the afterloader includes:

a drive system for controlling movement of the control element through the conduit, and a controller configured to communicate with the verification element; and a signal conductor for conducting the signal between the verification element and the controller.

22. The brachytherapy verification system of claim 21, wherein the controller is configured to communicate with one or more of an imaging system, a treatment planning system, a treatment delivery system, or a tracking system.

23. The brachytherapy verification system of claim 22, wherein the controller integrates the signal transmitted by the verification element with at least one of imaging data received from the imaging system or electromagnetic tracking data received from the tracking system.

24. The brachytherapy verification system of claim 21, wherein the verification element includes an optical element, wherein the reference marker has an optical property that is different than an optical property of the conduit, and wherein the verification element is configured to detect the optical property of the reference marker in order for the system to determine the proximity of the verification element to the reference marker.

25. The brachytherapy verification system of claim 21, wherein the verification element includes an electronic element or a coil, and wherein the verification element is configured to detect a change in an electromagnetic property of the reference marker in order for the system to determine the proximity of the verification element to the reference marker.

* * * * *

UNITED STATES PATENT AND TRADEMARK OFFICE
CERTIFICATE OF CORRECTION

PATENT NO. : 10,293,178 B2
APPLICATION NO. : 14/565807
DATED : May 21, 2019
INVENTOR(S) : Frits De Vries and Adriaan Van Appeldoorn Page 1 of 1

It is certified that error appears in the above-identified patent and that said Letters Patent is hereby corrected as shown below:

In the Claims

In Column 19, Line 41 (Claim 6), after "brachytherapy," delete "radiotherapy."

In Column 20, Line 34 (Claim 17), after "brachytherapy" delete "radiotherapy."

Signed and Sealed this
Seventeenth Day of September, 2019

Andrei Iancu
*Director of the United States Patent and Trademark Office*